US012780765B2

(12) United States Patent
Azam et al.

(10) Patent No.: US 12,780,765 B2
(45) Date of Patent: Nov. 3, 2026

(54) METHOD FOR PURIFYING LINEAR ALPHA OLEFINS

(71) Applicant: SABIC GLOBAL TECHNOLOGIES B.V., Bergen op Zoom (NL)

(72) Inventors: Shahid Azam, Riyadh (SA); Ashim Kumar Ghosh, Riyadh (SA); Vinu Viswanath, Riyadh (SA); Bander Bawareth, Riyadh (SA); Zheng Liu, Riyadh (SA); Aspi Kersasp Kolah, Riyadh (SA); Debashis Chakraborty, Bangalore (IN); Andrei Merenov, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 205 days.

(21) Appl. No.: 18/724,806

(22) PCT Filed: Dec. 22, 2022

(86) PCT No.: PCT/EP2022/087666
§ 371 (c)(1),
(2) Date: Jun. 27, 2024

(87) PCT Pub. No.: WO2023/126331
PCT Pub. Date: Jul. 6, 2023

(65) Prior Publication Data

US 2025/0100956 A1 Mar. 27, 2025

(30) Foreign Application Priority Data

Dec. 27, 2021 (EP) .................................... 21217782

(51) Int. Cl.
*C07C 6/04* (2006.01)
*C07C 7/00* (2006.01)
*C07C 7/05* (2006.01)
*C07C 7/148* (2006.01)

(52) U.S. Cl.
CPC ................ *C07C 7/05* (2013.01); *C07C 7/005* (2013.01); *C07C 7/1485* (2013.01); *C07C 7/14875* (2013.01); *C07C 2521/04* (2013.01); *C07C 2529/06* (2013.01); *C07C 2531/08* (2013.01)

(58) Field of Classification Search
CPC .............. C07C 6/04; C07C 7/05; C07C 7/005
See application file for complete search history.

(56) References Cited

U.S. PATENT DOCUMENTS 4,217,461 A * 8/1980 Ward ...................... C07C 11/08 585/800
4,697,040 A 9/1987 Williamson et al.
5,789,646 A 8/1998 Romera et al.
5,852,220 A 12/1998 Järvelin et al.
7,041,865 B2 5/2006 Doll et al.
8,562,921 B2 10/2013 Gadewar
9,018,427 B2 4/2015 Gadewar et al.
9,174,920 B1 11/2015 Panchal et al.
2003/0004385 A1* 1/2003 Gartside .................. B01J 37/14 585/670
2003/0009070 A1 1/2003 Doll et al.
2010/0099934 A1* 4/2010 Gartside ............... C07C 11/107 585/314
2011/0130604 A1* 6/2011 Gartside ................ B01D 3/146 585/324
2019/0345080 A1* 11/2019 Rallapalli .............. B01D 3/143
2022/0002215 A1* 1/2022 Hamilton ................ C07C 7/005
2024/0025822 A1 1/2024 Windler et al.

FOREIGN PATENT DOCUMENTS

DE 102006057856 A1 6/2008
EP 0673352 B1 4/1999
EP 2029701 B1 8/2015
RU 2206557 C1 6/2003
WO WO-2017115305 A1 * 7/2017 ............ B01D 3/141

OTHER PUBLICATIONS

Hussain et al. "Design method for the feasibility and technical evaluation of side-reactor column configurations" Chemical Engineering and Processing—Process Intensification, v. 144 (Oct. 2019), 8 pgs.
International Search Report for PCT/EP2022/087666, mailed Mar. 27, 2023, 4 pgs.
Baur R. and Krishna R. Distillation column with reactive pump arounds: an alternative to reactive distillation. Chem. Eng. Proc. 43, 2004, 435-445.
Budi H. Bisowarno B.H., Tian Y.C., Tadé M.O. Application of side reactors on ETBE reactive distillation. Chem. Eng. J. 99, 2004, 35-43.
Hussain A., Minh L.Q. and Lee M. Intensification of the ethylbenzene production process using a column configured with a side reactor. Chem. Engg. Proc.: Process Intensification. 122, 2017, 204-212.
Hussain A., Riaz A., Qyyum M.A. and Lee M. Design trade-offs in a column with side-reactor configuration for improving selectivity in multiple reaction systems. Chem. Eng. Proc. 134, 2018a, 86-96.

(Continued)

*Primary Examiner* — Randy Boyer
(74) *Attorney, Agent, or Firm* — Womble Bond Dickinson (US) LLP

(57) ABSTRACT

The disclosure provides a method of purifying a linear alpha olefin product, the method including feeding a linear alpha olefin feed stream comprising the linear alpha olefin product and at least one impurity into a distillation column, the distillation column having a plurality of stacked stages; withdrawing a side stream from at least one of said plurality of stacked stages; feeding the side stream into a reactor containing an isomerization catalyst to convert at least a portion of the at least one impurity from a first isomer to a second isomer, producing a reactor product stream having a reduced content of the first isomer; returning the reactor product stream to a stage of the distillation column; and withdrawing an overhead stream from the distillation column comprising the linear alpha olefin product and having a reduced content of the at least one impurity.

20 Claims, 7 Drawing Sheets

(56) References Cited

OTHER PUBLICATIONS

Hussain A. and Lee M. Optimal design of an intensified column with side-reactor configuration for the methoxy-methylheptane process. Chem. Eng. Res. Design. 136, 2018b, 11-24.
Hussain A., Chaniago Y.D., Riaza A. and Lee M. Significance of operating pressure on process intensification in a distillation with side-reactor configuration Sep. Pur. Tech. 213, 2019b, 533-544.
Jakobsson K., Pyhalahti A., Pakkanen S., Keskinen K. and Aittamaa J. Modelling of a side reactor configuration combining reaction and distillation. Chem. Eng. Sci. 57, 2002, 1521-1524.
Kaymak D.B. and Luyben W.L. Design of Distillation Columns with External Side Reactors. Ind. Eng. Chem. Res. 43, 2004, 8049-8056.
Kaymak D.B. and Luyben W.L. Optimum Design of a Column/Side Reactor Process. Ind. Eng. Chem. Res. 46, 2007, 5175-5185.
Kolah A.K., Lira C.T., Miller D.J., Prindle J.C. and Panchal C.B. Reactive distillation using external side reactors for synthesis of tri-ethyl citrate. 9th European Congress of Chemical Engineering and 2nd European Congress of Applied Biotechnology, The Hague, Netherlands, Apr. 21-25, 2013.
Kolah A.K., Lira C.T., Miller D.J., Prindle J.C. and Panchal C.B. Reactive distillation using external side reactors for synthesis of bio-renewable organic acid esters. A.I.Ch.E. Spring Conference, San Antonio, TX, USA, May 1, 2013.
Kolah A.K., Lira C.T., Miller D.J., Doctor R., Prindle J.C. and Panchal C.B. Reactive Distillation Using External Side Reactors for Synthesis of Tri-Ethyl Citrate. A.I.Ch.E. Spring Meeting, New Orleans, LA, USA, Apr. 1, 2014.
Pappu S., Kolah A.K., Lira C.T. and Miller D.J. Methyl stearate transesterification with n-butanol: Process intensification using distillation with external side reactors. A.I.Ch.E. Annual Conference, Minneapolis, MN, USA, Oct. 16-20, 2011.
Schoenmakers H. and Buehler W.K. Distillation column with external reactors—an alternative to the reaction column. German Chem. Eng. 5, 1982, 292-296.
Tsai R.C., Cheng J.K., Huang H.P. Yu C.C., Shen Y.S. and Chen Y.T. Design and Control of the Side Reactor Configuration for Production of Ethyl Acetate. Ind. Eng. Chem. Res. 47, 2008, 9472-9484.
Ye J., Li J., Sha Y., Lin H. and Zhou D. Evaluation of Reactive Distillation and Side Reactor Configuration for Direct Hydration of Cyclohexene to Cyclohexanol. Ind. Eng. Chem. Res. 53, 2014, 1461-1469.

* cited by examiner

METHOD FOR PURIFYING LINEAR ALPHA OLEFINS

CROSS-REFERENCE TO RELATED APPLICATIONS

The present application is a 371 U.S. national stage application of International Application No. PCT/EP2022/087666, filed Dec. 22, 2022, which claims priority from European Application No. 21217782.8, filed Dec. 27, 2021, all of which are incorporated herein by reference in their entirety.

TECHNOLOGICAL FIELD

The present disclosure relates to methods for purifying a linear alpha olefin product stream from an oligomerization reaction.

BACKGROUND

Linear olefins are a class of hydrocarbons useful as raw materials in the petrochemical industry and among these the linear alpha olefins, unbranched olefins whose double bond is located at a terminus of the chain, form an important subclass. Linear alpha olefins can be converted to linear primary alcohols by hydroformylation. Hydroformylation can also be used to prepare aldehydes, which in turn can be oxidized to afford synthetic fatty acids, especially those with an odd carbon number, useful in the production of lubricants. Linear alpha olefins are also used in the production of detergents, such as linear alkylbenzenesulfonates, which are prepared by Fiedel-Crafts reaction of benzene with linear olefins followed by sulfonation. Another important use of linear alpha olefins relates to production of linear low-density polyethylene (LLDPE) through catalytic co-polymerization with ethylene.

Preparation of alpha olefins is based largely on oligomerization of ethylene, which has a corollary that the alpha-olefins produced have an even number of carbon atoms. Oligomerization processes for ethylene mainly utilize organoaluminum compounds or transition metals as catalysts. Oligomerization methods are typically carried out in the presence of a catalyst that includes a zirconium component, such as zirconium tetraisobutyrate, and an aluminum component as activator, such as ethyl aluminum sesquichloride. Typically, the effluent from the reactor used to produce the linear alpha olefins is directed to one or more distillation columns to separate the various fractions of linear alpha olefins.

It is desirable to purify the alpha olefin products of oligomerization reactions to a very high purity level, such as a purity level of greater than 99.5 mol %. Achieving such a high degree of purity can be challenging using conventional separation processes due to the presence of impurities with a boiling point very close to the boiling point of the target alpha olefin products. There remains a need in the art for improvements in separation processes for such products.

BRIEF SUMMARY

Example implementations of the present disclosure are directed to processes for purifying a linear alpha olefin product stream. In particular, the processes of the invention entail use of a least one side reactor positioned to receive at least a fraction of the flow through a distillation column, the side reactor containing an isomerization catalyst capable of converting at least one impurity from a first isomer to a second isomer, the second isomer being more easily separated from the target linear alpha olefin. In this manner, the side reactor can improve separation efficiency of the distillation column and enable purification of the target linear alpha olefin to very high purity levels.

The present disclosure includes, without limitation, the following embodiments.

Embodiment 1: A method of purifying a linear alpha olefin product, comprising: feeding a linear alpha olefin feed stream comprising the linear alpha olefin product and at least one impurity into a distillation column, the distillation column having a plurality of stacked stages; withdrawing a side stream from at least one of said plurality of stacked stages; feeding the side stream into a reactor containing an isomerization catalyst to convert at least a portion of the at least one impurity from a first isomer to a second isomer, producing a reactor product stream having a reduced content of the first isomer; returning the reactor product stream to a stage of the distillation column; and withdrawing an overhead stream from the distillation column comprising the linear alpha olefin product and having a reduced content of the at least one impurity.

Embodiment 2: The method of Embodiment1, wherein the at least one impurity is a branched olefin.

Embodiment 3: The method of Embodiment 1 or 2, wherein the linear alpha olefin product is 1-hexene and the at least one impurity is 2-ethyl-1-butene or an isomer thereof.

Embodiment 4: The method of any one of Embodiments 1-3, wherein the first isomer is 2-ethyl-1-butene and the second isomer is cis- or trans-3-methyl-2-pentene.

Embodiment 5: The method of any one of Embodiments 1-4, wherein the overhead stream comprises about 99.5 mol % 1-hexene or greater.

Embodiment 6: The method of any one of Embodiments 1-5, wherein the overhead stream comprises about 200 ppm or less of n-hexane.

Embodiment 7: The method of any one of Embodiments 1-6, wherein the overhead stream comprises about 0.15 mol % of 2-ethyl-1-butene or an isomer thereof or less.

Embodiment 8: The method of any one of Embodiments 1-7, wherein the isomerization catalyst is capable of converting about 80 mol % or greater of 2-ethyl-1-butene to the second isomer in about 1 hour at a pressure of about 1-10 bar, a temperature of about 45-100° C., and a Liquid Hourly Space Velocity of about 0.5-8.5 $h^{-1}$.

Embodiment 9: The method of any one of Embodiments 1-8, wherein about 3 mol % or less of 1-hexene is converted to a different isomer under the same reaction conditions.

Embodiment 10: The method of any one of Embodiments 1-9, wherein the isomerization catalyst comprises an alumina material, a zeolite material, or an ion exchange resin, such as a zeolite material with a molar ratio of silica-to-alumina in the range of 5 to 1000 or the range of 25 to 300.

Embodiment 11: The method of any one of Embodiments 1-10, wherein the distillation column is substantially free of catalyst material.

Embodiment 12: The method of any one of Embodiments 1-11, wherein the distillation column comprises about 150 stages or less.

Embodiment 13: The method of any one of Embodiments 1-12, wherein the operating temperature of the reactor is about 45° C. to about 100° C.

Embodiment 14: The method of any one of Embodiments 1-13, wherein the distillation column comprises an overhead condenser that produces a reflux stream returned to the distillation column, and wherein the reflux ratio is about 4 to about 20, such as about 7 to about 15.

Embodiment 15: The method of any one of Embodiments 1-14, wherein feeding the side stream in the reactor comprises feeding the side stream into a first reactor of a set of a first reactor and a second reactor positioned in parallel, such that the second reactor is available for regeneration of the isomerization catalyst while the first reactor is in use.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1:
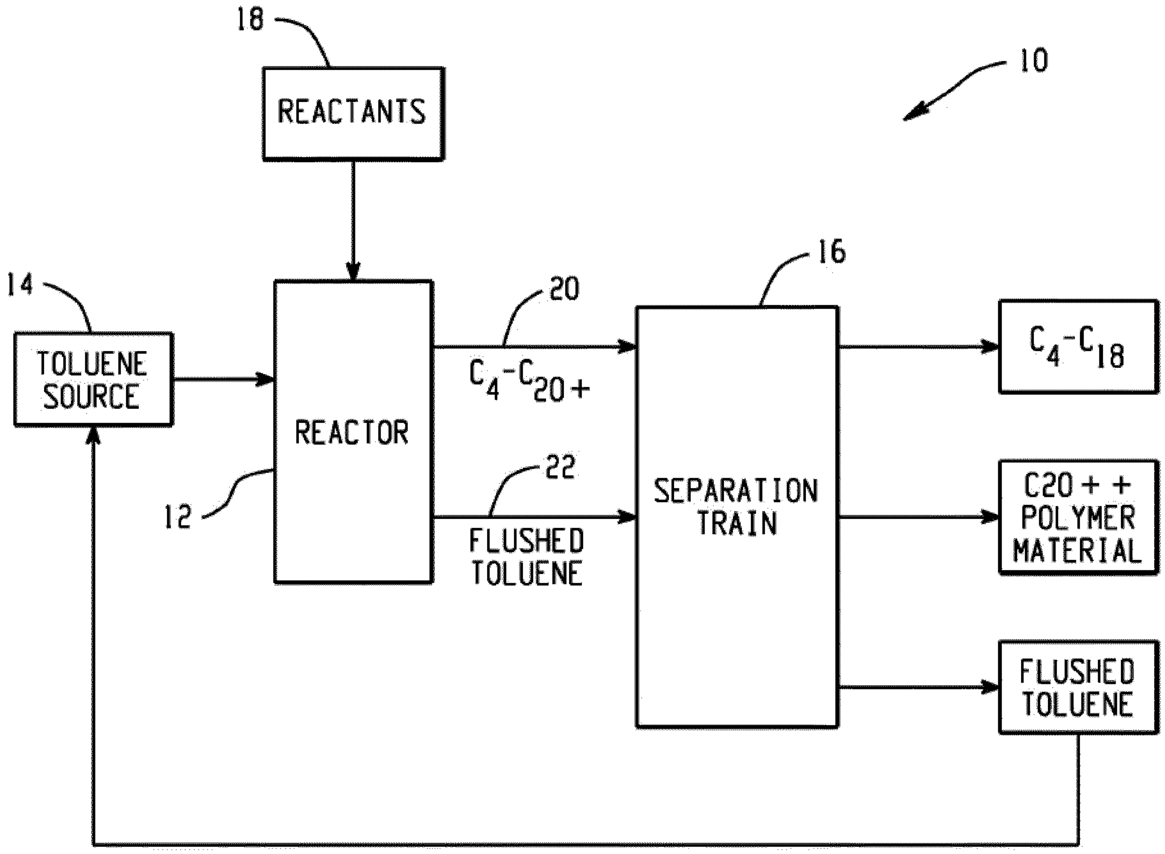
Figure 2:
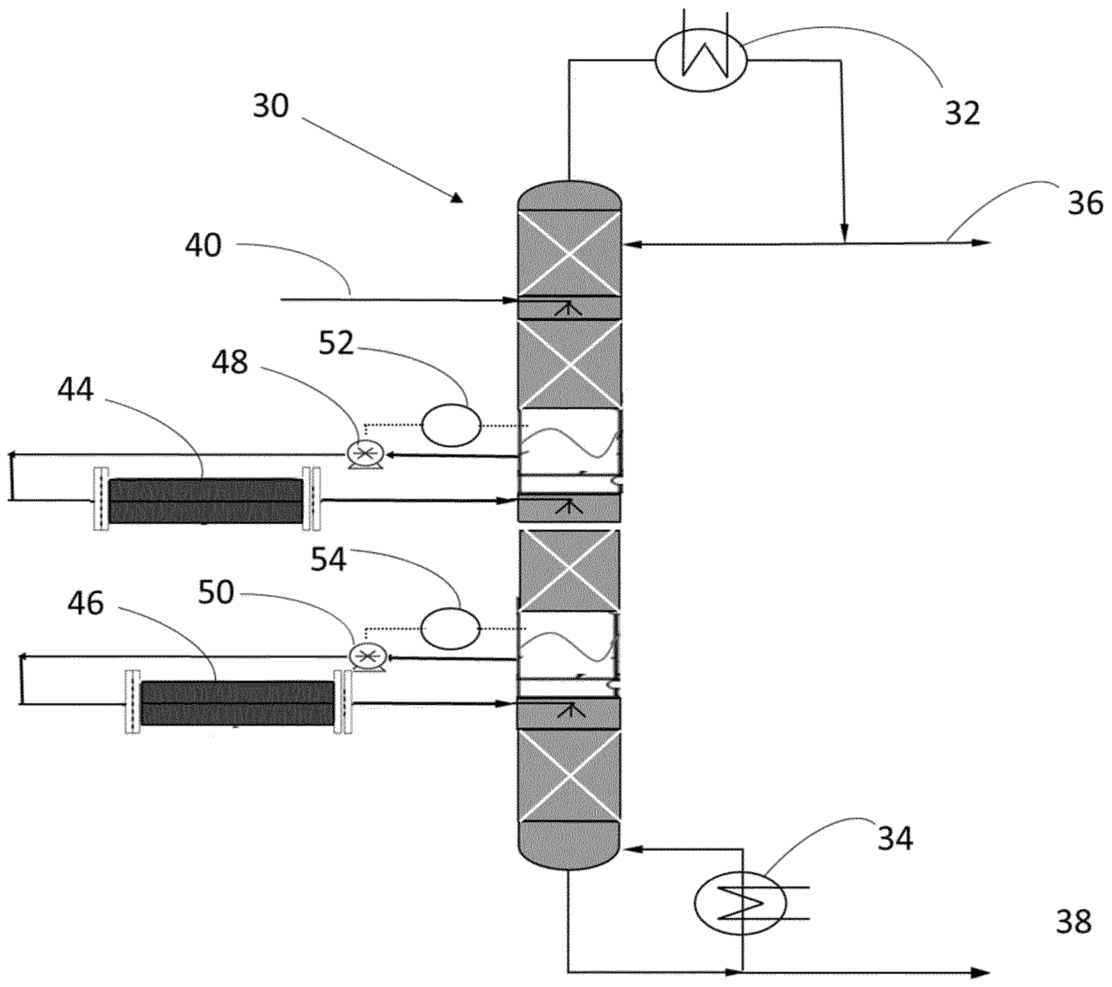
Figure 3:
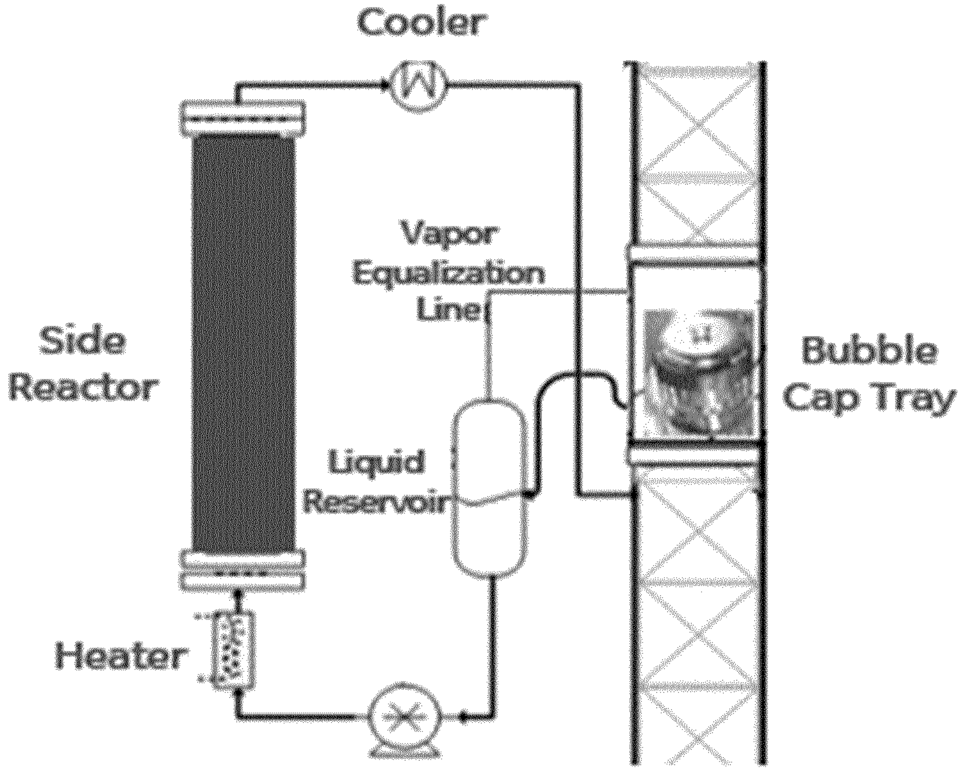
Figure 4:
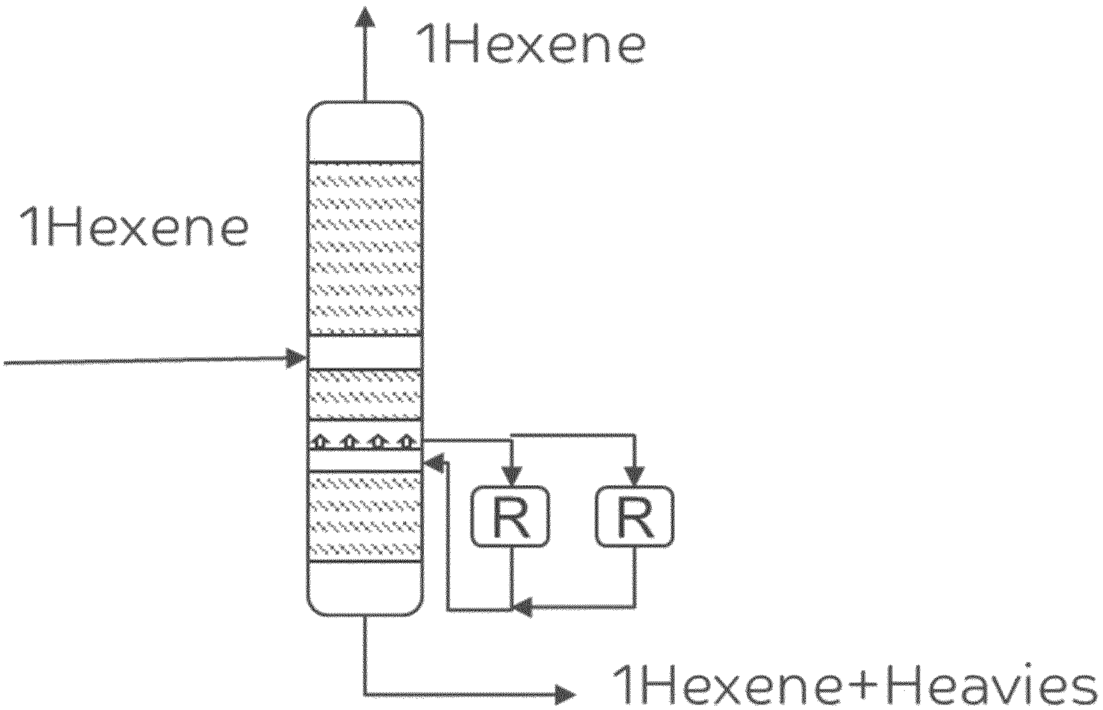
Figure 5:
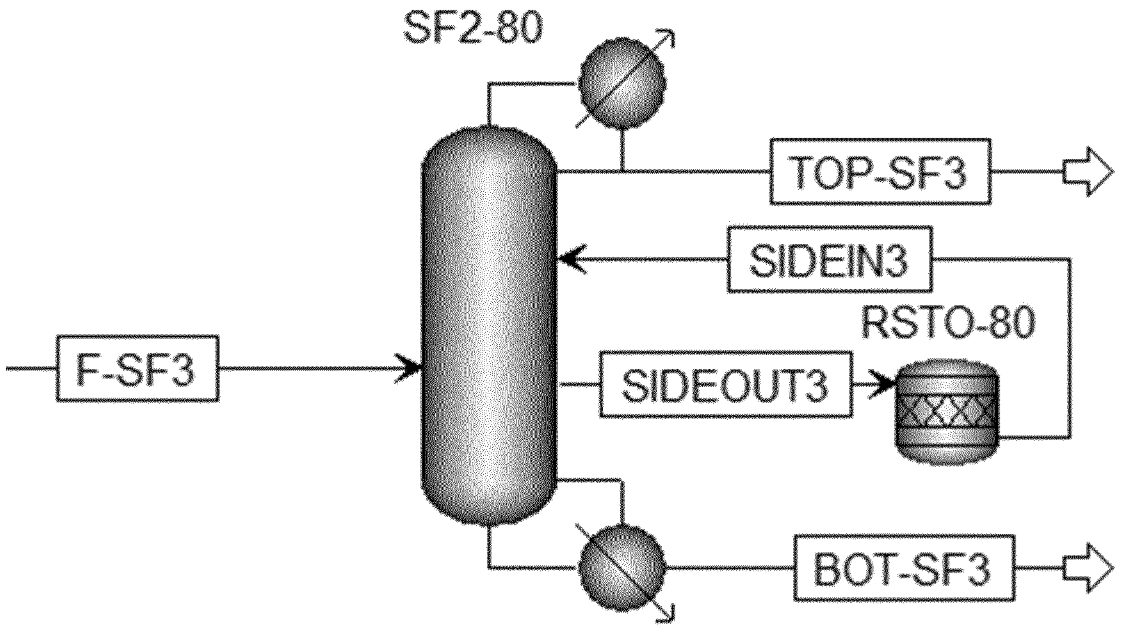
Figure 6:
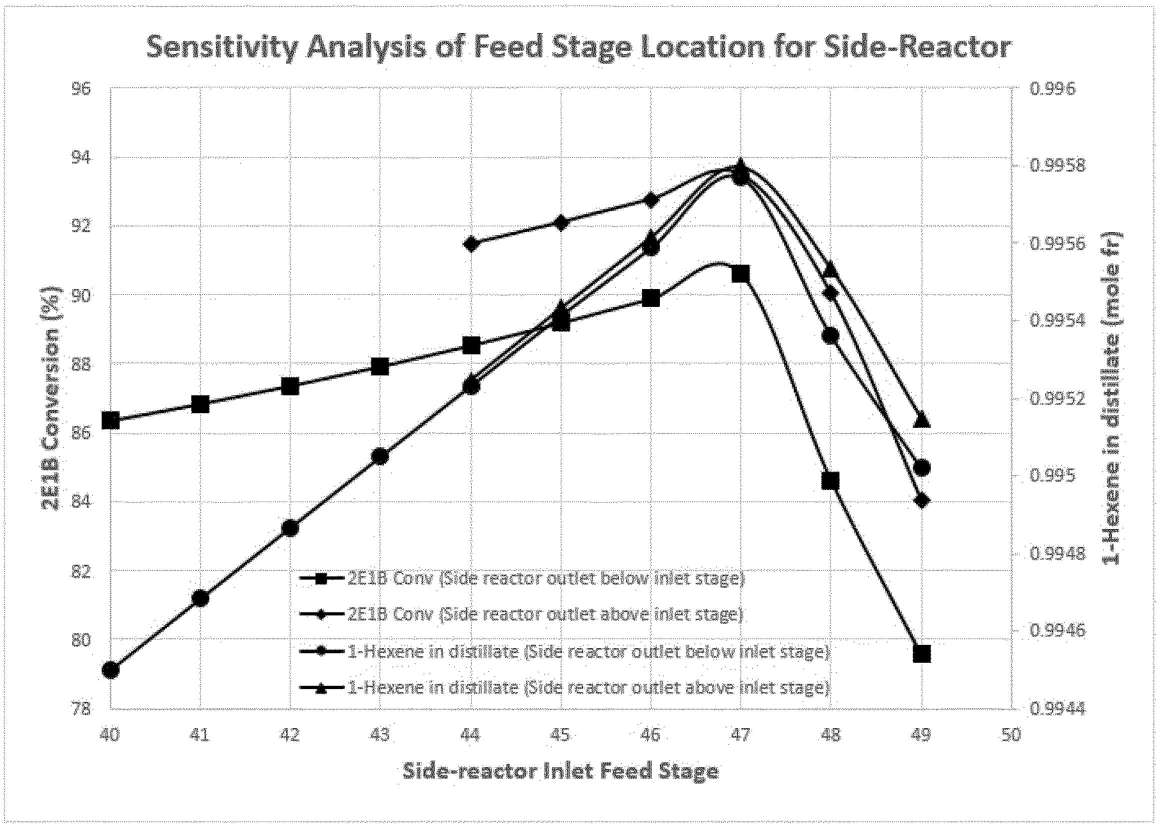
Figure 7:
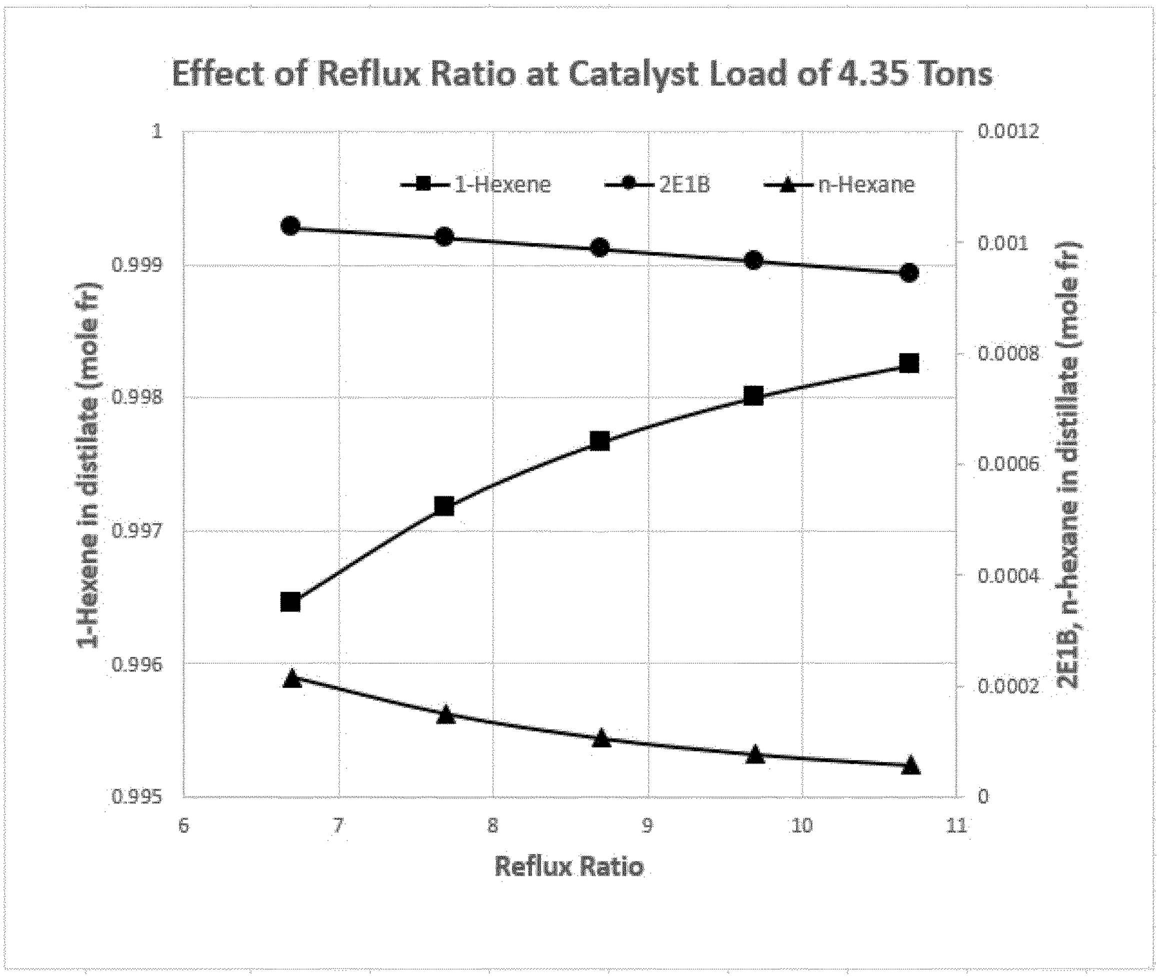

Having thus described aspects of the disclosure in the foregoing general terms, reference will now be made to the accompanying figures, which are not necessarily drawn to scale, and wherein:

FIG. 1 is a block diagram of an ethylene oligomerization system according to an example implementation of the present disclosure;

FIG. 2 is a schematic representation of an example embodiment of a distillation column with two side reactors according to the present disclosure;

FIG. 3 is a schematic representation of an example embodiment of a distillation column with one side reactor according to the present disclosure;

FIG. 4 is a schematic representation of an example embodiment of a distillation column with two side reactors positioned in parallel according to the present disclosure;

FIG. 5 is schematic representation of an example embodiment of a distillation column with a single side reactor used for Aspen Plus simulation according to the present disclosure;

FIG. 6 graphically illustrates the results of a simulation of the system arrangement of FIG. 5 to determine the optimal location for a side reactor according to one embodiment; and FIG. 7 graphically illustrates the results of a simulation of the system arrangement of FIG. 5 to determine impact of reflux ratio on product purity.

DETAILED DESCRIPTION

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

Unless specified otherwise or clear from context, references to first, second or the like should not be construed to imply a particular order. A feature described as being above another feature (unless specified otherwise or clear from context) may instead be below, and vice versa; and similarly, features described as being to the left of another feature else may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like.

As used herein, unless specified otherwise or clear from context, the "or" of a set of operands is the "inclusive or" and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. Further, the articles "a" and "an" mean "one or more," unless specified otherwise or clear from context to be directed to a singular form.

Ethylene Oligomerization Process and System

Linear alpha olefins (LAOs) are olefins with a chemical formula $C_xH_{2x}$, distinguished from other mono-olefins with a similar molecular formula by linearity of the hydrocarbon chain and the position of the double bond at the primary or alpha position. Linear alpha olefins comprise a class of industrially important alpha-olefins, including 1-butene, 1-hexene, 1-octene, 1-decene, 1-dodecene, 1-tetradecene, 1-hexadecene, 1-octadecene, and higher blends of $C_{20}$-$C_{24}$, $C_{24}$-$C_{30}$, and $C_{20}$-$C_{30}$ olefins. Linear alpha olefins are useful intermediates for the manufacture of detergents, synthetic lubricants, copolymers, plasticizers, and many other important products.

Existing processes for the production of linear alpha olefins typically rely on the oligomerization of ethylene. For example, linear alpha olefins can be prepared by the catalytic oligomerization of ethylene in the presence of a Ziegler-Natta-type catalyst or non-Ziegler-Natta-type catalyst.

Oligomerization can occur at temperatures of 10 to 200° C., for example, 20 to 100° C., for example, 50 to 90° C., for example, 55 to 80° C., for example, 60 to 70° C. Operating pressures can be 1 to 5 MegaPascals (MPa), for example, 2 to 4 MPa. The process can be continuous and mean residence times can be 10 minutes to 20 hours, for example 30 minutes to 4 hours, for example, 1 to 2 hours. Residence times can be chosen so as to achieve the desired conversion at high selectivity.

The process can be conducted in solution using an inert solvent, which is advantageously non-reactive with the catalyst composition. Examples of desirable organic solvents can include, but are not limited to, aromatic hydrocarbon solvents which can be unsubstituted or substituted with halogens, for example, toluene, benzene, xylene, monochlorobenzene, dichlorobenzene, chlorotoluene; aliphatic paraffin hydrocarbons, for example, pentane, hexane, heptane, octane, nonane, decane; alicyclic hydrocarbon compounds, for example, cyclohexane, decahydronaphthalene; and halogenated alkanes, for example, dichloroethane and dichlorobutane.

The process can be carried out in any reactor, such as a loop reactor, a plug-flow reactor, or a bubble column reactor. Oligomerization of ethylene is an exothermic reaction that can be cooled by a surplus flow of ethylene. The gases leaving at a top portion of the reactor can be cooled using a series of external coolers and condensers. The gas phase, after further cooling, can be recycled.

A bottom stream leaving the oligomerization reactor from a bottom portion can contain the active catalyst and unreacted ethylene. The reaction can be terminated to avoid undesirable side reactions by removing catalyst components from the organic phase through extraction with a caustic aqueous phase. Contact with the caustic aqueous phase can result in formation of nonreactive minerals corresponding to the catalyst components.

The organic phase, after passage through the catalyst removal system, can pass through a molecular sieve absorption bed and can then be fed to a distillation column to recover dissolved ethylene. Recovered ethylene can be recycled via an ethylene recycle loop while the product is fed to an intermediate vessel, after which the product can be fed to a separation section. In certain embodiments, the linear alpha olefins produced from the reactor can be directed into a separation train.

As illustrated in FIG. 1, the system 10 can include a reactor 12, a toluene (or other solvent) source 14, and a separation train 16. In normal production mode, reactants 18, such as ethylene, solvent, and a catalyst can be fed into the reactor 12 to produce linear alpha olefins and various impurities such as branched olefins and polymeric material. After the reaction, a discharge stream 20 can be directed into the separation train 16, wherein the discharge stream can include unreacted reactants, the produced linear alpha olefins, such as $C_4$-$C_{20+}$ olefins, solvent, catalyst, and various impurities. The separation train 16 can be configured to separate the linear alpha olefins from the solvent, catalyst, various impurities, and any unreacted ethylene. The separation train 16 can separate each linear alpha olefin, for example, yielding a $C_4$ stream, $C_6$ stream, $C_8$ stream, and so on. The separation train 16 can also separate the linear alpha olefins into certain fractions, such as $C_4$-$C_{10}$ fraction, $C_{11}$-$C_{17}$ fraction, $C_{18}$-$C_{20}$ fraction, $C_{20+}$ fractions, or any other desired fraction.

The linear alpha olefin product can be isolated using procedures including aqueous caustic catalyst quench followed by water washing and final product recovery by distillation. For example, the liquid product including the solvent (e.g., toluene) with the dissolved ethylene can be fed to the separation train 16 as noted above. In a first column, the unconsumed ethylene can be separated from the linear alpha olefin product and the solvent. The ethylene can be recycled back to the reactor. The heavier fractions can be routed to the subsequent separation section where the heavier fractions can be divided into the different linear alpha olefin fractions (e.g., C8, C10, >C12). The solvent can be recovered and also recycled back to the reactor.

Polymer fouling within the reactor can occur during the oligomerization reaction process. Such fouling is typically detected by, for example, reduced effluent flow rates, reduced internal condenser performance, increased differential pressure at various locations within the reactor, and the like. Such fouling can be treated by flushing the reactor with toluene or another solvent to remove polymeric material by-product. The flushed toluene comprising the polymeric material can be directed into a separation train comprising the linear alpha olefin reaction products. The polymeric material is soluble in at least one of the linear alpha olefins, such that the flushed toluene can exit the separation train essentially free of the polymeric material and can be recycled back to the toluene source for subsequent flushing of the reactor.

Integrated Distillation Column and Side Reactor

According to the present disclosure, the separation train will 16 will include at least one distillation column having at least one side reactor connected thereto. The type of distillation column may vary, with examples including columns with bubble cap trays, valve trays, or sieve trays.

The side reactor will include an isomerization catalyst adapted to convert at least one impurity entering the distillation column, such as a branched olefin, from a first isomer to a second isomer. It is advantageous for the boiling point of the second isomer to be further removed from the boiling point of the desired alpha olefin product as compared to the first isomer. Thus, the second isomer is more easily separated from the desired alpha olefin product by the distillation column as compared to the first isomer.

If the desired alpha olefin product is 1-hexene having a boiling point of 63.48° C., one example of a problematic impurity (i.e., the first isomer) is 2-ethyl-1-butene, which has a boiling point of 64.67° C. However, 2-ethyl-1-butene can be converted to a higher boiling point isomer (i.e., the second isomer) such as cis-/trans-3-methyl-2-pentene using an isomerization catalyst. This equilibrium limited reaction is shown below:

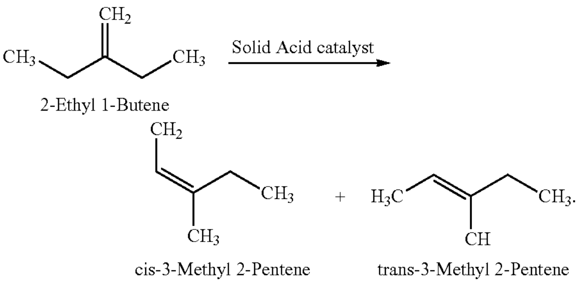

2-Ethyl 1-Butene
cis-3-Methyl 2-Pentene
trans-3-Methyl 2-Pentene

Example isomerization catalysts include an alumina material, a zeolite material, or an ion exchange resin. Suitable catalysts typically include acidic functional groups. Alumina catalysts are available, for example, under the trade name SELEXSORB® (e.g., SELEXSORB® CD or CDL) from BASF Corporation or third party suppliers. Ion exchange resin catalysts are available, for example, under the trade name AMBERLYST® (e.g., AMBERLYST® 15) from Dow Chemical Company or third party suppliers.

The zeolite catalyst material may vary. In some embodiments, the zeolite has a framework type selected from the group consisting of ABW, ACO, AEI, AEL, AEN, AET, AFI, AFN, AFO, AFR, AFS, AFT, AFX, AFY, AHT, APC, APD, ASV, ATN, ATO, ATS, ATT, ATV, AVL, AWO, AWW, BCT, BEA, BEC, BIK, BOF, BOG, BOZ, BPH, BRE, BSV, CAN, CAS, CDO, CFI, CGF, CGS, CHA, CHI, CLO, CON, CZP, DAC, DDR, DFO, DFT, DON, EAB, EDI, EEI, EMT, EON, EPI, ERI, ESV, ETR, EUO, EZT, FAU, FER, GIS, GME, GON, GOO, HEU, IFR, IFY, IHW, IMF, IRN, ISV, ITE, ITG, ITH, ITW, IWR, IWS, IWV, IWW, JBW, JRY, JSR, JST, KFI, LAU, LEV, LOV, LTA, LTF, LTL, LTN, MAZ, MEI, MEL, MER, MFI, MFS, MON, MOR, MOZ, MRE, MSE, MTF, MTT, MVY, MTW, MWF, MWW, NAB, NAT, NES, NPO, NPT, NSI, OBW, OFF, OKO, OSI, OSO, OWE, PAR, PAU, PCR, PHI, PON, PUN, RHO, RON, RRO, RSN, RTE, RTH, RWR, RWY, SAF, SAO, SAS, SAT, SAV, SBE, SBS, SBT, SCO, SEW, SFE, SFF, SFG, SFH, SFN, SFO, SFS, SFW, SGF, SIV, SOF, SOS, SSF, SSY, STF, STI, STO, STT, STW, SVR, SZR, TER, THO, TON, TSC, TUN, UEI, UFI, UOS, USI, UTL, UWY, VET, VFI, VNI, VSV, WIE, WEN, YUG, ZON, and mixtures or intergrowths thereof. In some embodiments, the zeolite comprises a framework type selected from the group consisting of AEI, BEA (Beta zeolites), CHA (chabazite), FAU (zeolite Y), FER (ferrierite), MFI (ZSM-5) and MOR (mordenite). Non-limiting examples of zeolites having these structures include chabazite, faujasite, zeolite Y, ultrastable zeolite Y, Beta zeolite, mordenite, silicalite, zeolite X, and ZSM-5.

The molar ratio of silica-to-alumina ("SAR") of the zeolite can vary over a wide range. For instance, the zeolite may have a SAR of from about 1 to about 1000. In one or more embodiments, the zeolite has a SAR molar ratio in the range of about 1, about 2, about 5, about 8, about 10, about 15, about 20, or about 25, to about 30, about 35, about 40, about 45, about 50, about 60, about 70, about 80 about 90, about 100, about 150, about 200, about 260, about 300, about 400, about 500, about 750 or about 1000 (e.g., about 10 to about 150 or about 20 to about 80). In certain embodiments, the zeolite material has a molar ratio of silica-to-alumina in the range of 5 to 1000 or the range of 25 to 300.

In certain embodiments, the isomerization catalyst can be characterized based on how much of the undesirable first isomer is converted to the second isomer. For example, in certain embodiments, the isomerization catalyst is capable of converting about 80 mol % or greater of 2-ethyl-1-butene (e.g., about 85 mol % or greater or about 90 mol % or greater or about 95 mol % or greater) to the second isomer in about 1 hour at a pressure of about 1-10 bar, a temperature of about 45-100° C., and a Liquid Hourly Space Velocity of about 0.5-8.5 $h^{-1}$. In some embodiments, about 3 mol % or less of 1-hexene (e.g., about 2 mol % or less or about 1 mol % or less) is converted to a different isomer under the same reaction conditions noted above.

The one or more side reactors can be operated, for example, as either plug flow reactors (otherwise known as tubular reactors) or continuous stirred-tank reactors (CSTR), and can be operated at temperatures and pressures that are independent of the distillation column operating temperature and pressure. The 1-hexene feed containing impurities can be fed to a tubular reactor in either upflow or downflow mode. In some embodiments, the feed stream is fed in upflow mode.

External side reactors are extremely useful when reaction conditions (e.g., temperature and pressure) for the catalyst are out of sync with desired distillation conditions. This process configuration is also extremely useful when a slow reactions requiring a large quantity of catalyst must be carried out. Conventional reactive distillation columns can typically only hold up to 20 to 40% by column volume of catalyst. Placing the catalyst in a side reactor avoids this limitation associated with reactive distillation processes. Typical operating temperature of the side reactor is in the range of about 40 to about 100° C., such as about 50 to about 70° C. The amount of catalyst in the side reactor can vary. In certain embodiments, the catalyst charge is about 3,000 to about 6,000 kg catalyst per side reactor, such as about 4,000 to about 5,000 kg.

Since the catalyst is located outside of the distillation column, regeneration of the catalyst can be accomplished more easily as compared to reactive distillation columns. It can be advantageous to use two external side reactors configured in parallel such that one reactor can be in service while the other reactor undergoes regeneration. An example regeneration process involves passing nitrogen gas at elevated temperature through the catalyst bed, such a nitrogen at a temperature of about 200° C. or higher, or about 250° C. or higher, or about 280° C. or higher (e.g., about 250 to about 300° C.).

Given the advantages of placing the isomerization catalyst outside the distillation column, in certain embodiments, the distillation column utilized in the present disclosure can be described as substantially or completely free of catalyst material, meaning the distillation column includes less than 1% by volume catalyst, or less than 0.5% by volume catalyst, or 0% by volume catalyst, within the column.

An example implementation of a distillation column with integrated side reactor is shown in FIG. 2. As shown, the separation train can include a distillation column 30, which typically includes a condenser 32 as a top stage and a reboiler 34 as a bottom stage. A distillate stream 36 leaves the top of the column as a product stream. A bottoms stream 38 also leaves the column. A feed stream 40 enters the column at a desired feed stage, which may vary. The feed stream 40 will typically include an alpha olefin product in need of further purification, along with one or more impurities, such as branched olefins. The reflux ratio of the distillation column can vary, with an example range being about 4 to about 20, such as about 7 to about 15.

The number of side reactors in fluid communication with the distillation column 30 may vary. Various embodiments will have from one to ten side reactors. In FIG. 2, two side reactors, 44 and 46, are shown. As shown, each side reactor, 44 and 46, is positioned to withdraw liquid from a stage of the distillation column 30 using a pump, 48 and 50, which can be controlled using a respective controller, 52 and 54, such as a level indicator controller.

FIG. 3 provides a more detailed view of one example embodiment of a side reactor 60 integrated with a distillation column 62, shown in partial sectional view. As shown, a liquid reservoir holding pot 64 can be used to hold liquid exiting the distillation column upstream of the pump 66 used to pump the liquid through the side reactor 60. A vapor pressure equalization line 68 can extend from the top of the holding pot 64 to the vapor headspace of the distillation column tray 70, which is shown as being a bubble cap tray only by way of example. Optionally, the system can include a pre-heater 72 upstream of the side reactor 60, as well as a cooler 74 downstream from the side reactor. Although not shown, it is possible for any desired heating/cooling of the streams entering or leaving the side reactor to be achieved through heat exchange with the column feed stream to increase thermal efficiency of the process.

The flow rate entering the side reaction can vary, and in particular, can be any fraction of the liquid flow in the column. In addition, the relative location of the stage from which liquid is drawn to feed the side reactor and the stage to which the effluent from the side reactor is returned can vary. The liquid can be withdrawn and returned to the same stage or returned to an adjacent stage or a stage further removed from the withdrawal stage. Thus, the number of stages between the withdrawal stage and the return stage can be 0 or any number from 1 to 100 or even higher. Liquid can be withdrawn from multiple stages and fed to the same reactor or multiple reactors.

As noted above, two side reactors placed in parallel can be integrated with the distillation column. An example of such an embodiment is shown in FIG. 4, where a 1-hexene feed stream enters a distillation column having two side reactors in parallel labeled with an R. The use of parallel reactors allows one reactor to be taken off-line for regeneration when the isomerization catalyst becomes fouled or otherwise deactivated without disrupting operation of the distillation column. Purified 1-hexene exits the top of the column with a majority of the impurities leaving as a bottoms stream.

The feed stream to the column can vary in composition, but is typically at least 96 mol % or at least 98 mol % 1-hexene (e.g., about 96 mol % to about 98.5 mol % or about 98 mol % to about 98.5 mol %) and at least 0.5 mol % or at least 0.8 mol % 2-ethyl-1-butene (e.g., about 0.5 mol % to about 1.5 mol % or about 0.8 mol % to about 1.2 mol %).

Use of a side reactor as contemplated herein can enable purification of 1-hexene or other linear alpha olefins to a purity of about 99.5 mol % or greater in the distillation column overhead stream. In certain embodiments, the overhead product stream from the distillation column is characterized by very low impurity content, such as about 0.3 mol % or less, or about 0.2 mol % or less, or about 0.15 mol % or less of branched olefins, such as 2-ethyl-1-butene. Where the target linear alpha olefin is 1-hexene, in certain embodiments, the overhead product stream is also characterized by very low n-hexane content, such as about 200 ppm or less or about 150 ppm or less n-hexane.

Use of a side reactor as contemplated in this disclosure can reduce the number of stages that might otherwise be required to achieve very high degrees of purity for certain linear alpha olefins, such as 1-hexene. For example, in certain embodiments, the number of distillation stages required to achieve a high degree of linear alpha olefin purity (e.g., a purity of about 99.5 mol % or greater) is about 150 stages or less or about 120 stages or less (e.g., about 80 to about 150 stages).

This technology is broadly applicable to isomerization reactions of C6 compounds as described herein, but also applicable for other reactions which are equilibrium limited. For example, such other reactions include isomerization reactions of other linear alpha olefins, metathesis reactions of C2 to C12 olefins, etherification reactions of C4 and C5 olefins with alcohols (e.g., methanol, ethanol, or isoamylalcohol) to form gasoline additives which increase octane number of the fuel, esterification, acetalization, and the like.

EXPERIMENTAL

Example 1

A series of lab reactor tests were conducted using a tubular reactor with various isomerization catalysts to determine feasibility of using such catalysts to convert 2-ethyl-1-butene (2E1B) to a different isomer, such as cis- or trans-3-methyl-2-pentene. Conversion percentages (mol %) were determined for both 2E1B and 1-hexene (1H) under the test conditions shown in Table 1 in terms of pressure (P), temperature (T), Liquid Hourly Space Velocity (LHSV), and residence time (TOS). The tested catalysts included various zeolites, alumina materials and one ion exchange resin.

TABLE 1

| | Test Conditions | | | | | |
|---|---|---|---|---|---|---|
| | P, | T, | LHSV, | TOS, | Conv (%) at | |
| Catalyst | psig | ° C. | $h^{-1}$ | h | 2E1B | 1H |
| ZSM-5 (SAR 23) | 1.5 | 45 | 8.57 | 2.97 | 99.05 | 21.1 |
| ZSM-5 (SAR 50) | 1.5 | 45 | 8.57 | 3.03 | 99.44 | 2.59 |
| ZSM-5 (SAR 50) | 1.5 | 45 | 3 | 3.43 | 50.55 | 0.46 |
| ZSM-5 (SAR 80) | 1.5 | 45 | 8.57 | 3.06 | 97.78 | 8.53 |
| ZSM-5 (SAR 280) | 1.5 | 50 | 5.14 | 2.92 | 97.67 | 1.19 |
| Ferrierite (SAR 20) | 1.5 | 45 | 8.57 | 3.09 | 99.46 | 9.63 |
| Zeolite Y (SAR 20) | 1.5 | 45 | 8.57 | 3.15 | 99.65 | 11.1 |
| Zeolite Y (SAR 60) | 1.5 | 45 | 8.57 | 2.91 | 98.16 | 19.45 |
| Selexsorb CD | 1.5 | 45 | 8.57 | 2.99 | 94.55 | 0 |
| Selexsorb CD | 1.5 | 45 | 3 | 2.92 | 89.52 | 0.01 |
| Selexsorb CD | 1.5 | 45 | 8.57 | 2.88 | 67.56 | 0 |
| Selexsorb CD | 1.5 | 45 | 8.57 | 2.94 | 79.94 | 0.02 |
| Selexsorb CDL | 1.5 | 45 | 8.57 | 2.91 | 17.18 | 0 |
| Actisorb 100-1 Alumina | 1.5 | 45 | 8.57 | 2.94 | 1.46 | 0 |
| Amberlyst-15 | 1.5 | 45 | 8.57 | 2.89 | 97.58 | 1.89 |

The results are also shown in Table 1. All of the tested catalysts were able to convert at least a portion of 2E1B to a more desirable isomer. However, several catalysts were not particularly selective for the 2E1B conversion and also converted a significant amount of 1-hexene to a different isomer, which is undesirable. The highest performing catalysts include, for example, ZSM-5 zeolite (particularly at higher SAR), SELEXSORB CD, and the ion exchange resin AMBERLYST-15.

Example 2

Process simulation studies were performed using Aspen Plus. The simulated process is shown schematically in FIG. 5, wherein F-SF3 is a 1-hexene feed stream, SF2-80 is a distillation column having 81 theoretical stages, TOP-SF3 is the overhead product stream, BOT-SF3 is the bottoms stream, and RSTO-80 is the side reactor receiving inlet flow SIDEOUT3 from the distillation column and returning SIDEIN3 to the distillation column. Simulation studies were performed to study the optimal location for the one side reactor configuration and it was observed that the optimal feed location of the side reactor is on Stage 47 with the liquid returned to the column on Stage 48. The simulated feed stream was 98.15 mol % 1-hexene and 0.99 mol % 2E1B. Results of this study are shown in FIG. 6.

Further simulation studies were performed to study the effect of reflux ratio on the 1-hexene purity using a fixed catalyst charge of 4,347 kg in the side reactor and the same simulated fee stream noted above. Results are shown in FIG. 7, where it can be seen that increase in reflux ratio increases the 1-hexene purity in the product stream with simultaneous decrease of n-hexane impurity.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

Many modifications and other implementations of the disclosure will come to mind to one skilled in the art to which this disclosure pertains having the benefit of the teachings presented in the foregoing descriptions and the associated figures. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. A method of purifying a linear alpha olefin product, comprising:

feeding a linear alpha olefin feed stream comprising the linear alpha olefin product and at least one impurity into a distillation column, wherein the at least one impurity is a branched olefin, the distillation column having a plurality of stacked stages;

withdrawing a side stream from at least one of said plurality of stacked stages;

feeding the side stream into a reactor containing an isomerization catalyst to convert at least a portion of the at least one impurity from a first isomer to a second isomer, producing a reactor product stream having a reduced content of the first isomer;

returning the reactor product stream to a stage of the distillation column; and withdrawing an overhead stream from the distillation column comprising the linear alpha olefin product and having a reduced content of the at least one impurity.

2. The method of claim 1, wherein the linear alpha olefin product is 1-hexene and the at least one impurity is 2-ethyl-1-butene or an isomer thereof.

3. The method of claim 2, wherein the first isomer is 2-ethyl-1-butene and the second isomer is cis- or trans-3-methyl-2-pentene.

4. The method of claim 2, wherein the overhead stream comprises about 99.5 mol % 1-hexene or greater.

5. The method of claim 2, wherein the overhead stream comprises about 200 ppm or less of n-hexane.

6. The method of claim 2, wherein the overhead stream comprises about 0.15 mol % of 2-ethyl-1-butene or an isomer thereof or less.

7. The method of claim 2, wherein the isomerization catalyst is capable of converting about 80 mol % or greater of 2-ethyl-1-butene to the second isomer in about 1 hour at a pressure of about 1-10 bar, a temperature of about 45-100° C., and a Liquid Hourly Space Velocity of about 0.5-8.5 $h^{-1}$.

8. The method of claim 7, wherein about 3 mol % or less of 1-hexene is converted to a different isomer under the same reaction conditions.

9. The method of claim 1, wherein the isomerization catalyst comprises an alumina material, a zeolite material, or an ion exchange resin.

10. The method of claim 1, wherein the distillation column is substantially free of catalyst material.

11. The method of claim 1, wherein the distillation column comprises about 150 stages or less.

12. The method of claim 1, wherein the operating temperature of the reactor is about 45° C. to about 100° C.

13. A method of purifying a linear alpha olefin product, comprising:

feeding a linear alpha olefin feed stream comprising the linear alpha olefin product and at least one impurity into a distillation column, the distillation column having a plurality of stacked stages;

withdrawing a side stream from at least one of said plurality of stacked stages;

feeding the side stream into a reactor containing an isomerization catalyst to convert at least a portion of the at least one impurity from a first isomer to a second isomer, producing a reactor product stream having a reduced content of the first isomer;

returning the reactor product stream to a stage of the distillation column; and withdrawing an overhead stream from the distillation column comprising the linear alpha olefin product and having a reduced content of the at least one impurity, wherein the distillation column comprises an overhead condenser that produces a reflux stream returned to the distillation column, and wherein the reflux ratio is about 4 to about 20.

14. The method of claim 1, wherein feeding the side stream in the reactor comprises feeding the side stream into a first reactor of a set of a first reactor and a second reactor positioned in parallel, such that the second reactor is available for regeneration of the isomerization catalyst while the first reactor is in use.

15. The method of claim 9, wherein the isomerization catalyst comprises a zeolite material with a molar ratio of silica-to-alumina in the range of 5 to 1000.

16. The method of claim 15, wherein the isomerization catalyst comprises a zeolite material with a molar ratio of silica-to-alumina in the range of 25 to 300.

17. The method of claim 13, wherein the reflux ratio is about 7 to about 15.

18. The method of claim 13, wherein the linear alpha olefin product is 1-hexene and the at least one impurity is 2-ethyl-1-butene or an isomer thereof.

19. The method of claim 13, wherein the overhead stream comprises about 99.5 mol % 1-hexene or greater, about 200 ppm or less of n-hexane, and about 0.15 mol % of 2-ethyl-1-butene or an isomer thereof or less.

20. The method of claim 13, wherein the isomerization catalyst comprises an alumina material, a zeolite material, or an ion exchange resin.

* * * * *